United States Patent
Bailey, Sr. et al.

(10) Patent No.: US 12,186,120 B2
(45) Date of Patent: Jan. 7, 2025

(54) METHODS AND SYSTEMS FOR X-RAY IMAGING AND LABELING

(71) Applicant: IDEXX Laboratories, Inc., Westbrook, ME (US)

(72) Inventors: Michael Q. Bailey, Sr., Export, PA (US); Scott Bender, South Portland, ME (US); Patrick Raymond Doyle, Old Orchard Beach, ME (US); Pavan Durgempudi, Portland, ME (US); Benjamin Litchfield, Portland, ME (US); David Steines, Scarborough, ME (US); Benjamin Schestopol, Scarborough, ME (US)

(73) Assignee: IDEXX Laboratories, Inc., Westbrook, ME (US)

( * ) Notice: Subject to any disclaimer, the term of this patent is extended or adjusted under 35 U.S.C. 154(b) by 0 days.

(21) Appl. No.: 18/438,691

(22) Filed: Feb. 12, 2024

(65) Prior Publication Data
US 2024/0180511 A1    Jun. 6, 2024

Related U.S. Application Data

(62) Division of application No. 17/141,893, filed on Jan. 5, 2021, now Pat. No. 11,918,401.
(Continued)

(51) Int. Cl.
*A61B 6/50*     (2024.01)
*G06F 18/243*   (2023.01)
(Continued)

(52) U.S. Cl.
CPC ............ *A61B 6/508* (2013.01); *G06F 18/243* (2023.01); *G06N 20/00* (2019.01); *G06T 7/0014* (2013.01);
(Continued)

(58) Field of Classification Search
None
See application file for complete search history.

(56) References Cited

U.S. PATENT DOCUMENTS

| 6,694,047 B1 | 2/2004 | Farrokhnia et al. |
| 7,529,394 B2 | 5/2009 | Krishnan et al. |
| (Continued) | | |

OTHER PUBLICATIONS

Arsomngern et al., "Computer-Aided Diagnosis for Lung Lesion in Companion Animals from X-ray Images Using Deep Learning Techniques, " 2019 IEEE 10th International Conference on Awareness Science and Technology (iCAST), Oct. 23-25, 2019 (Year: 2019).*

(Continued)

*Primary Examiner* — Soo Shin
(74) *Attorney, Agent, or Firm* — McDonnell Boehnen Hulbert & Berghoff LLP

(57) ABSTRACT

An example method includes capturing, via an x-ray machine, a plurality of x-ray images of a patient covering a number of different anatomy of the patient in any order, using a machine learning algorithm to process the plurality of x-ray images for identification of an anatomy in respective x-ray images of the plurality of x-ray images, associating a label with each of the plurality of x-ray images based on the identification of the anatomy, positioning each of the plurality of x-ray images upright based on a preset coordinate scheme for the anatomy, arranging the plurality of x-ray images into a predetermined order based on the species of the patient, and generating and outputting a data file including the plurality of x-ray images in the predetermined order, positioned upright, and labeled.

20 Claims, 7 Drawing Sheets

Related U.S. Application Data

(60) Provisional application No. 62/959,022, filed on Jan. 9, 2020.

(51) Int. Cl.
| | | |
|---|---|---|
| *G06N 20/00* | (2019.01) | |
| *G06T 7/00* | (2017.01) | |
| *G16H 15/00* | (2018.01) | |
| *G16H 30/20* | (2018.01) | |
| *G16H 30/40* | (2018.01) | |
| *G16H 50/20* | (2018.01) | |
| *G16H 70/20* | (2018.01) | |

(52) U.S. Cl.
CPC ............. *G16H 15/00* (2018.01); *G16H 30/20* (2018.01); *G16H 30/40* (2018.01); *G16H 50/20* (2018.01); *G16H 70/20* (2018.01); *G06T 2207/10116* (2013.01); *G06T 2207/20081* (2013.01); *G06T 2207/30004* (2013.01); *G06T 2207/30168* (2013.01); *G06V 2201/03* (2022.01)

(56) References Cited

U.S. PATENT DOCUMENTS

| | | | |
|---|---|---|---|
| 7,672,491 B2 | 3/2010 | Krishnan et al. | |
| 8,170,306 B2 | 5/2012 | Yu et al. | |
| 8,645,306 B2 | 2/2014 | Hammond | |
| 9,489,562 B2 | 11/2016 | Bayer | |
| 9,802,125 B1* | 10/2017 | Suskind | A63F 13/847 |
| 9,947,090 B2 | 4/2018 | Agam et al. | |
| 10,127,659 B2 | 11/2018 | Hsieh et al. | |
| 10,198,816 B2 | 2/2019 | Steigauf et al. | |
| 10,593,041 B1* | 3/2020 | Shaw | G06V 10/764 |
| 2018/0042566 A1 | 2/2018 | Roffe et al. | |
| 2018/0101645 A1 | 4/2018 | Sorenson et al. | |
| 2018/0149600 A1 | 5/2018 | Farrell | |
| 2019/0005684 A1 | 1/2019 | DeFauw et al. | |
| 2019/0340753 A1 | 11/2019 | Brestel et al. | |
| 2019/0340763 A1* | 11/2019 | Laserson | G06F 18/2321 |
| 2020/0273166 A1* | 8/2020 | Shaw | G06F 18/214 |
| 2024/0180511 A1* | 6/2024 | Bailey, Sr. | G06T 7/0014 |

OTHER PUBLICATIONS

International Search Report and Written Opinion prepared by the European Patent Office in International Application No. PCT/US2020/012196 dated Apr. 30, 2021.

Liew, "The future of radiology augmented with Artificial Intelligence: A strategy for success", European Journal of Radiology 102 (2018) pp. 152-156.

Patel et al., "Human-machine partnership with artificial intelligence for chest radiograph diagnosis", Nature partner Journals, npj Digital Medicine (2019) 2:111, https://doi.org/10.1038/s41746-019-0189-7.

Aboud et al. "Automatic classification of body parts X-ray images", Department of Software Engineering, Jerusalem College of Engineering, Jun. 25, 2009.

Maier, "A gentle introduction to deep learning in medical image processing", Friedrich-Alexander-University, Germany, Med Phys, (2019) https://doi.org/10.1016/j/zemedi.2018.12.003.

\* cited by examiner

↓
PROVIDING, VIA THE COMPUTING DEVICE, FEEDBACK FOR PROPER PROCEDURE ON HOW TO CAPTURE X-RAYS OF ANATOMY BASED ON CONTENT OF THE PLURALITY OF X-RAY IMAGES INCLUDING MORE ANATOMY THAN INTENDED ACCORDING TO THE LABEL OF THE PLURALITY OF X-RAY IMAGES ~ 332

FIG. 8

↓
COMPARING THE PLURALITY OF X-RAY IMAGES WITH A LISTING OF X-RAY IMAGES REQUIRED FOR A SELECTED PROCEDURE ~ 334

↓
PROVIDING, VIA THE COMPUTING DEVICE, FEEDBACK IN REAL-TIME THAT IS INDICATIVE OF A MISSING X-RAY REQUIRED FOR THE SELECTED PROCEDURE ~ 336

FIG. 9

↓
ANALYZING THE PLURALITY OF X-RAY IMAGES TO DETERMINE THAT AT LEAST ONE X-RAY IMAGE INCLUDES CONTENT OF A SECOND SPECIES ~ 338

↓
PROVIDING, VIA THE COMPUTING DEVICE, FEEDBACK THAT IS INDICATIVE OF PROPER PROCEDURE ON HOW TO CAPTURE X-RAYS ~ 340

FIG. 10

↓
RECEIVING INFORMATION INDICATING AN AMOUNT OF EXPOSURE USED BY THE X-RAY MACHINE TO CAPTURE THE PLURALITY OF X-RAY IMAGES ~ 342

↓
ANALYZING THE PLURALITY OF X-RAY IMAGES TO DETERMINE A QUALITY OF THE PLURALITY OF X-RAY IMAGES ~ 344

↓
PROVIDING, VIA THE COMPUTING DEVICE, FEEDBACK INDICATIVE OF AN OPTIMAL EXPOSURE SETTING FOR THE X-RAY MACHINE TO CAPTURE SUBSEQUENT X-RAY IMAGES ~ 346

FIG. 11

METHODS AND SYSTEMS FOR X-RAY IMAGING AND LABELING

CROSS-REFERENCE TO RELATED APPLICATION

The present disclosure is a divisional of and claims priority to U.S. application Ser. No. 17/141,893, filed on Jan. 5, 2021, which claims priority to U.S. provisional application No. 62/959,022, filed on Jan. 9, 2020, the entire contents of each of which are herein incorporated by reference.

FIELD

The present disclosure relates generally to methods for capturing and labeling x-ray images, and more particularly, to automatically identifying features of x-ray images for autonomous labeling and post-processing.

BACKGROUND

Many radiology instruments used by veterinarians typically assume a pre-determined "shot order" protocol for x-rays to be taken of a patient, such as, e.g. skull, thorax, and then abdomen. When the x-rays are taken in this protocol, the instruments automatically label the first x-ray as skull, the second x-ray as thorax, the third x-ray as abdomen, and so forth, without any image analysis to verify content of the x-ray (or to verify that the x-ray is skull, thorax, abdomen, etc.).

In practice, however, the veterinarian often captures x-ray images in an order other than the pre-determined optimal protocol, and then needs to go into the patient records and rename/reclassify the images. In some instances, the veterinarian may want an alternate angle or an improved image, and thus, the image may be retaken. As such, the order may not be used specifically as listed. In other instances, for example, the patient may be an animal and may move during the procedure resulting in an altogether different order of images being taken.

Because the instrument is programmed to label images in a specific order regardless of the actual image taken in practice, when images are taken out of order, the images are not properly labeled. This can be a problem because the type of shot drives other image processing algorithms, and thus, when the image is not properly labeled, further image processing can be performed improperly.

Accordingly, a more effective system is needed for capturing and processing x-ray images that provides additional freedom for the veterinarian to work with the patients as needed during image capture.

SUMMARY

In an example, a method is described that comprises capturing, via an x-ray machine, a plurality of x-ray images of a patient covering a number of different anatomy of the patient in any order, and using a machine learning algorithm, via execution by a computing device, to process the plurality of x-ray images for identification of an anatomy in respective x-ray images of the plurality of x-ray images. The method also comprises associating, by the computing device, a label with each of the plurality of x-ray images based on the identification of the anatomy, wherein the label is selected from among a preset labeling scheme for anatomy based on a species of the patient. The method further comprises positioning each of the plurality of x-ray images upright based on a preset coordinate scheme for the anatomy, arranging the plurality of x-ray images into a predetermined order based on the species of the patient, and generating and outputting a data file including the plurality of x-ray images in the predetermined order, positioned upright, and labeled.

In another example, a system is described that comprises an x-ray machine to capture a plurality of x-ray images of a patient covering a number of different anatomy of the patient in any order, and a computing device having one or more processors and non-transitory computer readable medium storing instructions executable by the one or more processors to perform functions. The functions comprise using a machine learning algorithm to process the plurality of x-ray images for identification of an anatomy in respective x-ray images of the plurality of x-ray images, associating a label with each of the plurality of x-ray images based on the identification of the anatomy, wherein the label is selected from among a preset labeling scheme for anatomy based on a species of the patient, positioning each of the plurality of x-ray images upright based on a preset coordinate scheme for the anatomy, arranging the plurality of x-ray images into a predetermined order based on the species of the patient, and generating and outputting a data file including the plurality of x-ray images in the predetermined order, positioned upright, and labeled.

In still another example, an improved computer implemented method is described. In a computer implemented method for x-ray imaging and labeling comprising capturing, via an x-ray machine, a plurality of x-ray images of a patient covering a number of different anatomy of the patient in a predetermined shot order structure, and applying a preset label to each of the plurality of x-ray images according to the predetermined shot order structure independent of content of the plurality of x-ray images, the method comprises ceasing use of the predetermined shot order structure, enabling use of a free-form shot order structure, using a machine learning algorithm, via execution by a computing device, to process the plurality of x-ray images for identification of an anatomy in respective x-ray images of the plurality of x-ray images, and associating, by the computing device, a label with each of the plurality of x-ray images based on the identification of the anatomy, wherein the label is selected from among a preset labeling scheme for anatomy based on a species of the patient.

In still another example, an improved veterinary radiology system is described. In a veterinary radiology system that includes radiology image capture hardware and radiology image capture software, wherein the radiology image capture software is executable by one or more processors of a computing device and requires a predetermined shot order structure for capturing via the radiology image capture hardware a plurality of x-ray images of a patient covering a number of different anatomy so as to apply a preset label to each of the plurality of x-ray images according to the predetermined shot order structure independent of content of the plurality of x-ray images, the system comprises updated radiology image capture software executable by the one or more processors that enables free-form shot order structure for application of the preset labels to each of the plurality of x-ray images based on content of the plurality of x-ray images and independent of the free-form shot order structure.

In still a further example, a method is described of upgrading a veterinary radiology system at a location where companion animal radiology images are taken. The method comprises modifying or replacing radiology image capture software that had utilized a predetermined shot order structure but not a free-form shot order structure with radiology software that enables free-form shot order structure.

The features, functions, and advantages that have been discussed can be achieved independently in various examples or may be combined in yet other examples. Further details of the examples can be seen with reference to the following description and drawings.

BRIEF DESCRIPTION OF THE FIGURES

The novel features believed characteristic of the illustrative examples are set forth in the appended claims. The illustrative examples, however, as well as a preferred mode of use, further objectives and descriptions thereof, will best be understood by reference to the following detailed description of an illustrative example of the present disclosure when read in conjunction with the accompanying drawings, wherein:

FIG. 8 shows another flowchart of additional functions that may be used with the method in FIG. 3, according to an example implementation.

FIG. 9 shows another flowchart of additional functions that may be used with the method in FIG. 3, according to an example implementation.

FIG. 10 shows another flowchart of additional functions that may be used with the method in FIG. 3, according to an example implementation.

FIG. 11 shows another flowchart of additional functions that may be used with the method in FIG. 3, according to an example implementation.

DETAILED DESCRIPTION

Figure 1:
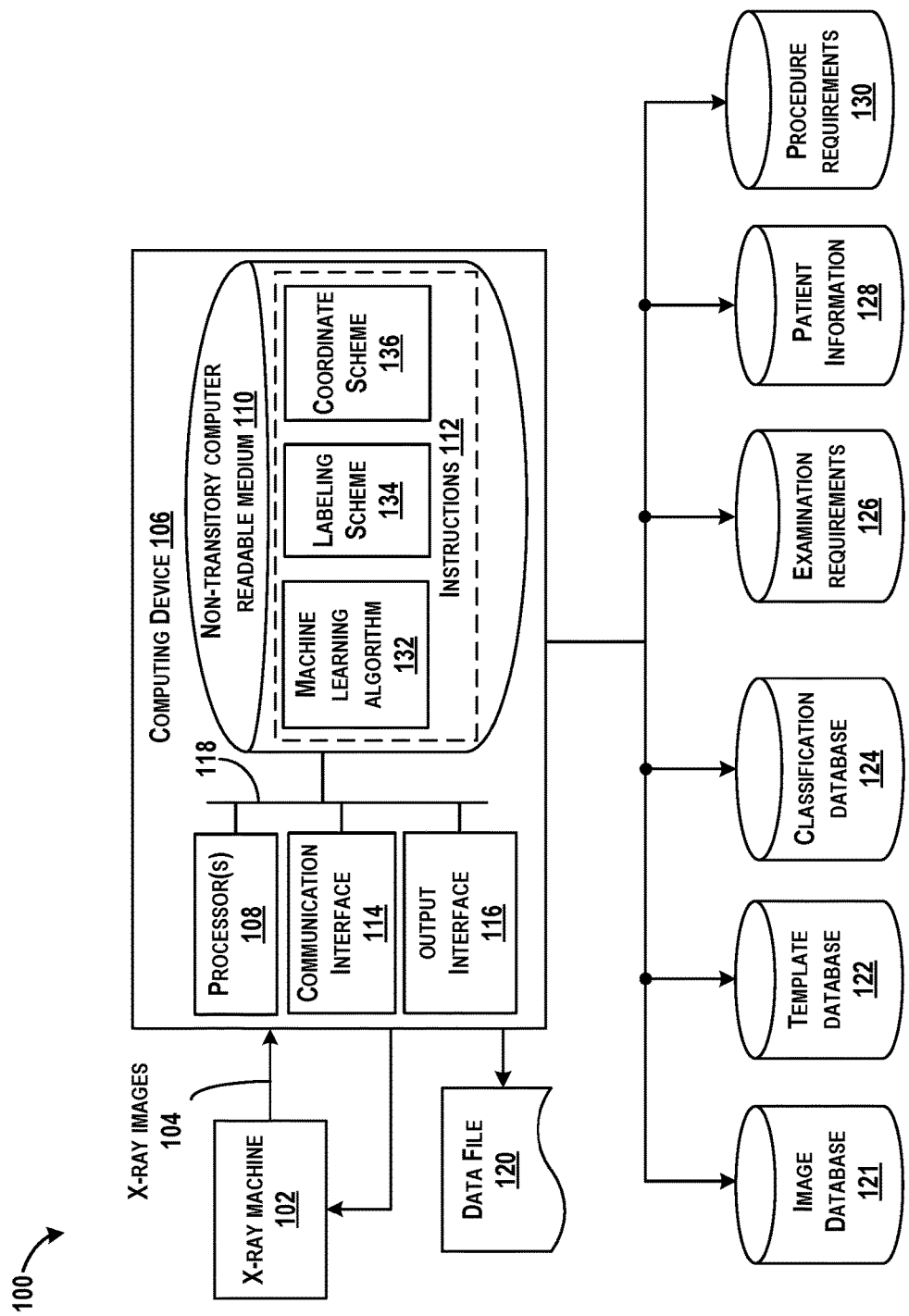
FIG. 1 illustrates an example system including an x-ray machine to capture a plurality of x-ray images (and other medical data) of a patient covering a number of different anatomy of the patient in any order and a computing device, according to an example implementation.

Disclosed examples will now be described more fully hereinafter with reference to the accompanying drawings, in which some, but not all of the disclosed examples are shown. Indeed, several different examples may be described and should not be construed as limited to the examples set forth herein. Rather, these examples are described so that this disclosure will be thorough and complete and will fully convey the scope of the disclosure to those skilled in the art.

Within examples, methods for capturing and processing x-ray images are described that include capturing, via an x-ray machine, a plurality of x-ray images of a patient covering a number of different anatomy of the patient in any order. A machine learning algorithm can then be executed by a computing device to process the plurality of x-ray images for identification of an anatomy in respective x-ray images of the plurality of x-ray images, and the computing device associates a label with each of the plurality of x-ray images based on the identification of the anatomy. The plurality of x-ray images are positioned upright based on a preset coordinate scheme for the anatomy, arranged into a predetermined order based on the species of the patient, and an output data file is generated including the plurality of x-ray images in the predetermined order, positioned upright, and labeled.

The computing device can thus automatically classify and label the x-ray images that are captured in any order rather than requiring a predetermined shot order with predetermined labeling. Thus, initially at a veterinarian lab, for example, a technician can position a patient for x-rays, and cause the x-ray machine to capture images as desired in any order. The systems and methods are very beneficial to enable the technician to work closely with the patient and capture images as possible without forcing specific shots.

Machine learning algorithms are applied to classify and label the x-ray images, so as to apply a correct label to the image, and then to cause correct image processing to be applied. As a specific example, a machine learning algorithm can be executed to determine that the image is an x-ray of a skull, and then cause the image to be labeled as a skull. The algorithm is executed to perform an image classification of the image as a whole. To do so, supervised models and training images can be used initially to train the algorithm of examples of images that are labeled "skull". In some examples, an image may include portions of a skull and a thorax, and the anatomy that is more center/prominent in the image can be selected to determine an intent of the shot was for thorax.

Following classification, the computing device will reorganize the images into a predetermined order. For example, radiologists on-site prefer to read cases and analyze images in a given order (e.g., skull, thorax, abdomen, etc.).

Also, the computing device will execute machine learning algorithms to determine an orientation of the x-ray image, and cause a rotation of the image if needed. The algorithm is executed here to identify parts of anatomy in the image, and use rules to classify the orientation appropriately. For example, images should be oriented right-side up, and "head" up or left. This can include a sub-classification of the image, as compared to the classification of the image as a whole for label determination.

A resulting output file is generated with all images in the predetermined order, positioned upright, and labeled. The output file may be in a digital imaging and communications in medicine format (DICOM file format).

The systems and methods provide a solution to enable technicians to change from a predetermined shot order structure to a free-form short order structure. For instance, in a predetermined shot order structure, the software is configured to assign anatomical structures to radiology shots (e.g., images) in a particular, programmatic, predetermined order, such as, for example: 1) skull; 2) thorax; 3) abdomen; regardless of what images are actually taken. In contrast, new methods described herein are beneficial to provide the free-form shot order structure in which the software does not use a predetermined order, but rather analyzes a shot and assigns at least one anatomical structure to the shot based on the analysis.

Implementations of this disclosure provide technological improvements that are particular to computer technology, for example, those concerning analysis of x-ray images. Computer-specific technological problems, such as enabling labeling and classification of x-ray images, can be wholly or partially solved by implementations of this disclosure. For example, implementation of this disclosure allows for correct labeling of x-ray images, and avoidance of following a predetermined shot order. In practice, this enables a technician to repeat an x-ray, if desired, without an improper label being applied.

Similarly, this enables a technician to capture a shot when it is available, e.g., such as when the patient is laying in a manner where the abdomen is present and ready for image capture. For veterinarians working with animals, such freedom of workflow is extremely beneficial.

The systems and methods of the present disclosure further address problems particular to computer devices and x-ray imaging, for example, those concerning the post-processing of x-ray images. Images are processed based on an associated label, and thus, an incorrect label leads to incorrect processing. Furthermore, existing methods enable a veterinarian to capture an x-ray and manually label the image; however, many images receive a "miscellaneous" label resulting in unknown post-processing to be performed. These computing device-specific issues can be solved by implementations of the present disclosure in which x-ray images are auto-classified and labeled using machine learning algorithms.

Implementations of this disclosure can thus introduce new and efficient improvements in the ways in which x-ray images are analyzed resulting in workflow efficiencies due to automation of image classification and labeling.

Referring now to the figures, FIG. 1 illustrates an example system 100 including an x-ray machine 102 to capture a plurality of x-ray images 104 (and other medical data) of a patient covering a number of different anatomy of the patient in any order, and a computing device 106, according to an example implementation. The x-ray machine 102 is coupled to or in communication with the computing device 106 to output the x-ray images 104 to the computing device 106.

In some examples, the x-ray machine 102 is physically connected to the computing device 106 via a wired connection, and in other examples, a wireless connection may be used. In yet further examples, the computing device 106 may include a remote server residing in the cloud accessible via a network connection, such as the internet, a wireless area network (WAN), or a local area network (LAN), for example.

The terms "x-ray", "image" or "scan" or derivatives thereof refer to x-ray (XR), magnetic resonance imaging (MRI), computerized tomography (CT), sonography, cone beam computerized tomography (CBCT), or any output of a system or machine that produces a quantitative spatial representation of a patient or object. The x-ray machine 102 may be any type of imaging device (e.g., gamma camera, positron emission tomography (PET) scanner, computed tomography (CT) scanner, magnetic resonance (MR) imaging machine, ultrasound scanner, etc.) that generates x-ray images (e.g., native Digital Imaging and Communications in Medicine (DICOM) images) representative of the parts of the body (e.g., organs, tissues, etc.) to diagnose and/or treat a patient. X-ray images may include volumetric data including voxels associated with a part of the body captured in the medical image.

In a veterinarian context, in a lab a technician positioned the animal on a table, and traditionally selects a worklist of shots (e.g., skull, thorax, abdomen) for capture. In practice, the technician may capture a first skull shot, but may need to retake the shot due to movement of the patient. Thus, the worklist will not be in order. Existing x-ray machines and computing devices expect the shots to be made in the selected order.

Within examples, the computing device 106 has one or more processor(s) 108 and non-transitory computer readable medium 110 storing instructions 112 executable by the one or more processors 108 to perform functions for auto-classification and labeling of the x-ray images 104. The computing device 106 is shown as a stand-alone component in FIG. 1. In some other examples, the computing device 106 may be incorporated within the x-ray machine 102.

To perform functions noted above, the computing device 106 also includes a communication interface 114, an output interface 116, and each component of the computing device 106 is connected to a communication bus 118. The computing device 106 may also include hardware to enable communication within the computing device 106 and between the computing device 106 and other devices (not shown). The hardware may include transmitters, receivers, and antennas, for example.

The communication interface 114 may be a wireless interface and/or one or more wireline interfaces that allow for both short-range communication and long-range communication to one or more networks or to one or more remote devices. Such wireless interfaces may provide for communication under one or more wireless communication protocols, Bluetooth, WiFi (e.g., an institute of electrical and electronic engineers (IEEE) 802.11 protocol), Long-Term Evolution (LTE), cellular communications, near-field communication (NFC), and/or other wireless communication protocols. Such wireline interfaces may include an Ethernet interface, a Universal Serial Bus (USB) interface, or similar interface to communicate via a wire, a twisted pair of wires, a coaxial cable, an optical link, a fiber-optic link, or other physical connection to a wireline network. Thus, the communication interface 114 may be configured to receive input data from one or more devices, and may also be configured to send output data to other devices.

The non-transitory computer readable medium 110 may include or take the form of memory, such as one or more computer-readable storage media that can be read or accessed by the one or more processor(s) 108. The non-transitory computer readable medium 110 can include volatile and/or non-volatile storage components, such as optical, magnetic, organic or other memory or disc storage, which can be integrated in whole or in part with the one or more processor(s) 108. In some examples, the non-transitory computer readable medium 110 can be implemented using a single physical device (e.g., one optical, magnetic, organic or other memory or disc storage unit), while in other examples, the non-transitory computer readable medium 110 can be implemented using two or more physical devices. The non-transitory computer readable medium 110 thus is a computer readable storage, and the instructions 112 are stored thereon. The instructions 112 include computer executable code.

The one or more processor(s) 108 may be general-purpose processors or special purpose processors (e.g., digital signal processors, application specific integrated circuits, etc.). The one or more processor(s) 108 may receive inputs from the communication interface 114 (e.g., x-ray images), and process the inputs to generate outputs that are stored in the non-transitory computer readable medium 110. The one or more processor(s) 108 can be configured to execute the instructions 112 (e.g., computer-readable program instructions) that are stored in the non-transitory computer readable medium 110 and are executable to provide the functionality of the computing device 106 described herein.

The output interface 116 outputs information for reporting or storage (e.g., the data file 120), and thus, the output interface 116 may be similar to the communication interface 114 and can be a wireless interface (e.g., transmitter) or a wired interface as well.

The system 100 can also include or be coupled to a number of databases, such as an image database 121, a template database 122, a classification database 124, an examination requirements database 126, a patient information database 128, and a procedure requirements database 130. In FIG. 1, the additional databases are shown as separate components of the computing device 106; however, each database may alternatively be integrated within the computing device 106. Access of the databases further enables the computing device 106 to perform functions as described herein. Functionality and content of the databases is described below.

Within one example, in operation, when the instructions 112 are executed by the one or more processor(s) 108, the one or more processor(s) 108 are caused to perform functions including using a machine learning algorithm 132 to process the plurality of x-ray images 104 for identification of an anatomy in respective x-ray images of the plurality of x-ray images 104, associating a label with each of the plurality of x-ray images 104 based on the identification of the anatomy that is selected from among a preset labeling scheme 134 for anatomy based on a species of the patient, positioning each of the plurality of x-ray images 104 upright based on a preset coordinate scheme 136 for the anatomy, arranging the plurality of x-ray images 104 into a predetermined order based on the species of the patient, and generating and outputting a data file 120 including the plurality of x-ray images 104 in the predetermined order, positioned upright, and labeled. The data file 120 may be in a DICOM file format.

The machine learning algorithm 132 uses statistical models to identify anatomy of the x-ray images effectively without using explicit instructions, but instead, can rely on patterns and inferences. In one example, the machine learning algorithm 132 accesses the image database 121, which includes previously labeled x-ray images that are indexed using a multi-dimensional indexing scheme based on relevant features/parameters. In such examples, the features/parameters extracted from x-ray image under consideration can be compared to the feature data of labeled x-ray images in the image database 121 to identify particular anatomy or view, and help identify the label of the image captured.

In another example, the machine learning algorithm 132 can access the template database 122, which includes templates constructed using information obtained from the image database 121. For example, feature data over a plurality of known and labeled x-rays can be processed using statistical techniques to derive feature data for a template representative over the set of related cases. In this instance, the features/parameters extracted from an x-ray under consideration can be compared to the feature data for templates in the template database 122 to identify a particular anatomy or view, and to help identify the label of the x-ray captured.

In still another example, the machine learning algorithm 132 can access the classification database 124, which includes a knowledge base of training data that can be learned from the image database 121 and the template database 122 of previously labeled x-ray images.

The machine learning algorithm 132 can thus operate according to machine learning tasks as classified into several categories. In supervised learning, the machine learning algorithm 132 builds a mathematical model from a set of data that contains both the inputs and the desired outputs. The set of data is sample data known as "training data", in order to make predictions or decisions without being explicitly programmed to perform the task. For example, for determining whether an x-ray image is an abdomen shot, the training data for a supervised learning algorithm would include images with and without example abdomens for specific species, and each image would have a label (the output) designating whether it contained the abdomen. The training data for teaching the machine learning algorithm 132 may be acquired from prior x-ray classifications, for example.

In another category referred to as semi-supervised learning, the machine learning algorithm 132 develops mathematical models from incomplete training data, where a portion of the sample input does not have labels. A classification algorithm can then be used when the outputs are restricted to a limited set of values.

In another category referred to as unsupervised learning, the machine learning algorithm 132 builds a mathematical model from a set of data that contains only inputs and no desired output labels. Unsupervised learning algorithms are used to find structure in the x-ray images, such as grouping or clustering of data points. Unsupervised learning can discover patterns in the x-ray images, and can group the inputs into categories.

The machine learning algorithm 132 may be executed to identify anatomy in the x-ray image and then an appropriate label from the labeling scheme can be applied to the x-ray image. The type and amount of anatomy that is possible is a finite number, and thus, the machine learning algorithm 132 may classify the x-ray images into one of a selected number of groups, such as skull-neck, upper-limb, body-abdomen, lower-limb and other.

Alternative machine learning algorithms 132 may be used to learn and classify the x-ray images, such as deep learning though neural networks or generative models. Deep machine learning may use neural networks to analyze prior x-ray images through a collection of interconnected processing nodes. The connections between the nodes may be dynamically weighted. Neural networks learn relationships through repeated exposure to data and adjustment of internal weights. Neural networks may capture nonlinearity and interactions among independent variables without pre specification. Whereas traditional regression analysis requires that nonlinearities and interactions be detected and specified manually, neural networks perform the tasks automatically.

A convolutional neural network is a type of neural network. Layers in a convolutional neural network extract features from the input x-ray image. The deep learning learns features that are distinctive for classification. Convolution preserves spatial relationship between pixels of images by learning image features using small squares of input data (i.e., filter kernels for convoluting with an input image are used). The convolutional neural network is composed for instance of N convolutional layers, M pooling layers, and at least one fully connected layer.

Still other machine learning algorithms or functions can be implemented to identify anatomy of the x-ray images, such as any number of classifiers that receives input parameters and outputs a classification (e.g., attributes of the image). Support vector machine, Bayesian network, a probabilistic boosting tree, neural network, sparse auto-encoding classifier, or other known or later developed machine learning algorithms may be used. Any semi-supervised, supervised, or unsupervised learning may be used. Hierarchal, cascade, or other approaches may be also used.

In one example, to identify anatomy in the x-ray image, initially any detected anatomy in the image is first identified (using training data), and then bounding boxes are drawn around the anatomy (e.g., around abdomens, etc., to disambiguate edge cases). Using localization around specific portions of the images enables an improved training phase to better predict a whole image classification, for example.

The preset labeling scheme 134 may include a numbering of different labels available based on a species of the patient. For example, for a dog, the possible labels available may include skull, thorax, abdomen, and limbs. Based on identification of anatomy in the x-ray, e.g., a heart is identified, then the x-ray may be labeled as thorax.

The preset coordinate scheme 136 includes orientations of the x-ray images that are desired. For example, during imaging, the patient may move and an upside down image may be captured. The computing device 106 will then be able to re-orient the x-ray image to a correct orientation. This may include a further machine learning algorithm to be executed to identify location and orientation of the identified anatomy in the x-ray image such that rules can be executed to position the x-ray into the desired orientation.

Following, the computing device 106 arranges the plurality of x-ray images 104 into a predetermined order based on the species of the patient. In one example, the order is governed based on species, and for a dog, e.g., the order may be (1) skull, (2) abdomen, (3) limbs.

In other examples, an order may be based on an industry standard, such as arranging similar anatomy together (e.g., thorax together, abdomen together, etc.), or can also be user selectable.

In other examples, an order may be based on user preference, and requires input by a user to specify the desired order.

The data file 120 is then generated and output including the plurality of x-ray images 104 in the predetermined order, positioned upright, and labeled. The data file 120 then is provided for further image processing, which is dictated based on a respective label of each x-ray image of the plurality of x-ray images in the data file 120.

In one example, image processing includes examination by a radiology technician. In such instances, the computing device 106 can be configured to determine requirements of x-ray images for the species of the patient for qualification to submit for examination by access to the examination requirements database 126. For example, examination of x-rays for a dog may require submission of a skull shot, an abdomen shot, and a limbs shot. Without a full set of these different shots, the technician may be unable to diagnose or analyze the x-rays in a complete manner according to a submission query. Thus, the computing device 106 may be configured to filter the plurality of x-ray images for the x-ray images required for qualification to submit for examination, and based on the x-ray images required for qualification to submit for examination being available in the plurality of x-ray images, the computing device 106 generates and outputs the data file including the x-ray images required for qualification to submit for examination in the predetermined order, positioned upright, and labeled.

As a specific example, a thorax study for a dog may require two specific x-rays, and when the specific required x-rays are identified and labeled, the data file 120 can be generated and output to telemedicine. The radiology technicians have specific rules to follow for examinations and studies to be performed, and if the x-ray data file is missing images, the studies cannot be completed.

In another example, image processing includes associating patient identification information with the x-ray images. The computing device 106 can thus access the patient information database 128 to retrieve associated patient identification information. For example, based on the identification of the anatomy in respective x-ray images of the plurality of x-ray images 104, the computing device 106 can determine the species of the patient, and from the species of the patient, the computing device 106 can associate patient identification information with the plurality of x-ray images 104. The computing device 106 may further utilize timestamps of the x-rays cross referenced with scheduling to access the specific patient identification. The patient identification information may include species, breed, age, gender, or other information as available from the patient information management system (PIMS) that stores information in the patient information database 128. In some examples, however, it may be the case that the patient information is known and already associated with the x-ray images.

The patient identification information may further be beneficial to assist with the x-ray image identification. For example, the computing device 106 may be configured to associate patient identification information with the plurality of x-ray images 104 prior to identification of the x-ray images, and based on the patient identification information, the computing device 106 further determines the species of the patient. Following, the computing device 106 can execute the machine learning algorithm 132 to select a training data set for use by the machine learning algorithm 132 based on the species of the patient. The image database 121, the template database 122, and the classification database 124 all may have different types of training data per different type of species. The patient identification enables the species to be determined and the correct training data set to be used.

The computing device 106 may execute the instructions 112 to identify and label the x-ray images and generate outputs very quickly (e.g., executable in less than a second), and in some examples, the computing device 106 may provide real-time feedback to the technician at a time of image capture. As an example, in instances where the software classification or orientation processes were inconclusive, the computing device 106 may set a flag for a notification to the technician to request a new image (or to retake the x-ray in real-time while the patient is lying on the table).

The system 100 can be configured to provide other types of feedback as well. In one instance, the system 100 provides, via the computing device 106, feedback for proper procedure on how to capture x-rays of anatomy based on content of the plurality of x-ray images 104 including more anatomy than intended according to the label of the plurality of x-ray images 104. As an example, in instances in which the x-ray image has been identified as labeled as "head" or "skull", but the x-ray image includes a portion of the abdomen too, feedback can be provided on adjustments that can be made during image capture so that the x-ray focuses more directly on the skull. The feedback can be in the form of a textual notification or other feedback with images or links on a display to inform the technician of better x-ray capture practices.

In another example, feedback can include notifying the x-ray technician of the type of x-rays required for a selected procedure. The computing device 106 can thus access the procedure requirements database 130 to determine all shots, angles, orientations, etc., of the patient to capture for say, a thorax investigation. Thus, the computing device 106 may be able to compare the plurality of x-ray images 104 that are captured with a listing of x-ray images required for the selected procedure, and then provide feedback in real-time that is indicative of a missing x-ray required for the selected procedure. This enables the technician to capture the missing x-ray in real-time while the patient is lying on the x-ray table.

In yet another example, feedback can include changes to settings of the x-ray machine 102 so as to improve x-ray quality. For instance, the computing device 106 can receive from the x-ray machine 102 information indicating an amount of exposure used by the x-ray machine 102 to capture the plurality of x-ray images 104, analyze the plurality of x-ray images 104 to determine a quality of the plurality of x-ray images 104, and provide feedback indicative of an optimal exposure setting for the x-ray machine 102 to capture subsequent x-ray images. The optimal exposure would be, in many instances, a low dose exposure. An exposure index may be received with the image (e.g., histogram exposure) as metadata to determine exposure levels, for example.

In yet a further example, the feedback can focus on safety for the x-ray technician. For example, the species of the patient may be a first species (e.g., dog, cat, etc.), and the computing device 106 may analyze the plurality of x-ray images 104 to determine that at least one x-ray image includes content of a second species (e.g., human), and then provide feedback that is indicative of proper procedure on how to capture x-rays. In this example, it is preferable for the x-ray technician to avoid exposure to the x-rays so as not to capture in the x-ray image any portion of their hand or body.

In some instances, feedback can include calculation of an output score of the data file 120. The score can be indicative of how well the animal was positioned, for example, an image labeled abdomen also included portions of thorax. Alternatively, the score can be useful for determining the label to provide to the image, such as whether a probability of the image being for the thorax or abdomen increases or decreases based on position of the anatomy in the image. The score can be a probability that indicates some certainty with the label given for the image. In some examples where possible, the image can be shift to re-run through the model (e.g., perturb images) to generate a higher score for a given anatomy.

In further examples, the computing device 106 may execute the instructions 112 to identify and label the x-ray images and generate outputs at a time after a point of capture (e.g., not in real-time) to provide batch processing of images. In this manner, batches of images can be analyzed after imaging to assess the quality of the images, provide appropriate labeling, or generate scores for further analysis, for example.

Figure 2:
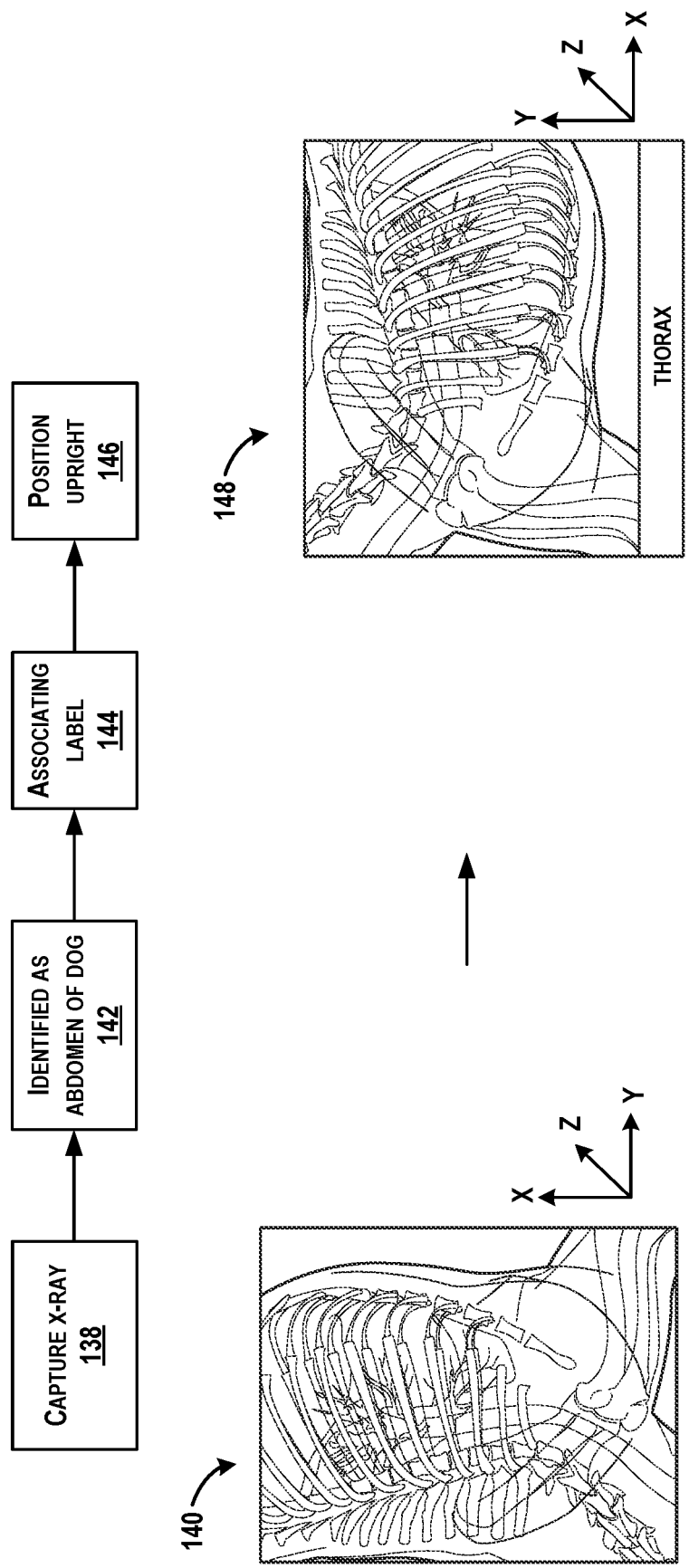
FIG. 2 illustrates an example workflow process for image capture and processing, according to an example implementation.

FIG. 2 illustrates an example workflow process for image capture and processing, according to an example implementation. Initially, at block 138, an x-ray is captured and an example x-ray image 140 is shown. Following, the computing device 106 executes the machine learning algorithm 132 to identify anatomy of the x-ray. In this example, at block 142, the x-ray is identified to include an abdomen of a dog. Following, the computing device 106 associates an appropriate label with the x-ray (e.g., abdomen), and then analyzes the x-ray for a desired orientation. Here, the x-ray image 140 was captured from an undesired orientation, which may be based according to a traditional x-y-z axis. Thus, at block 146, the computing device 106 rotates the x-ray image 140 to an upright position as shown by x-ray image 148 by rotating in the x-y plane and flipping the image about the y-axis. The upright position may be such that the x-ray image 148 is oriented right-side up, and "head" up or left.

Figure 3:
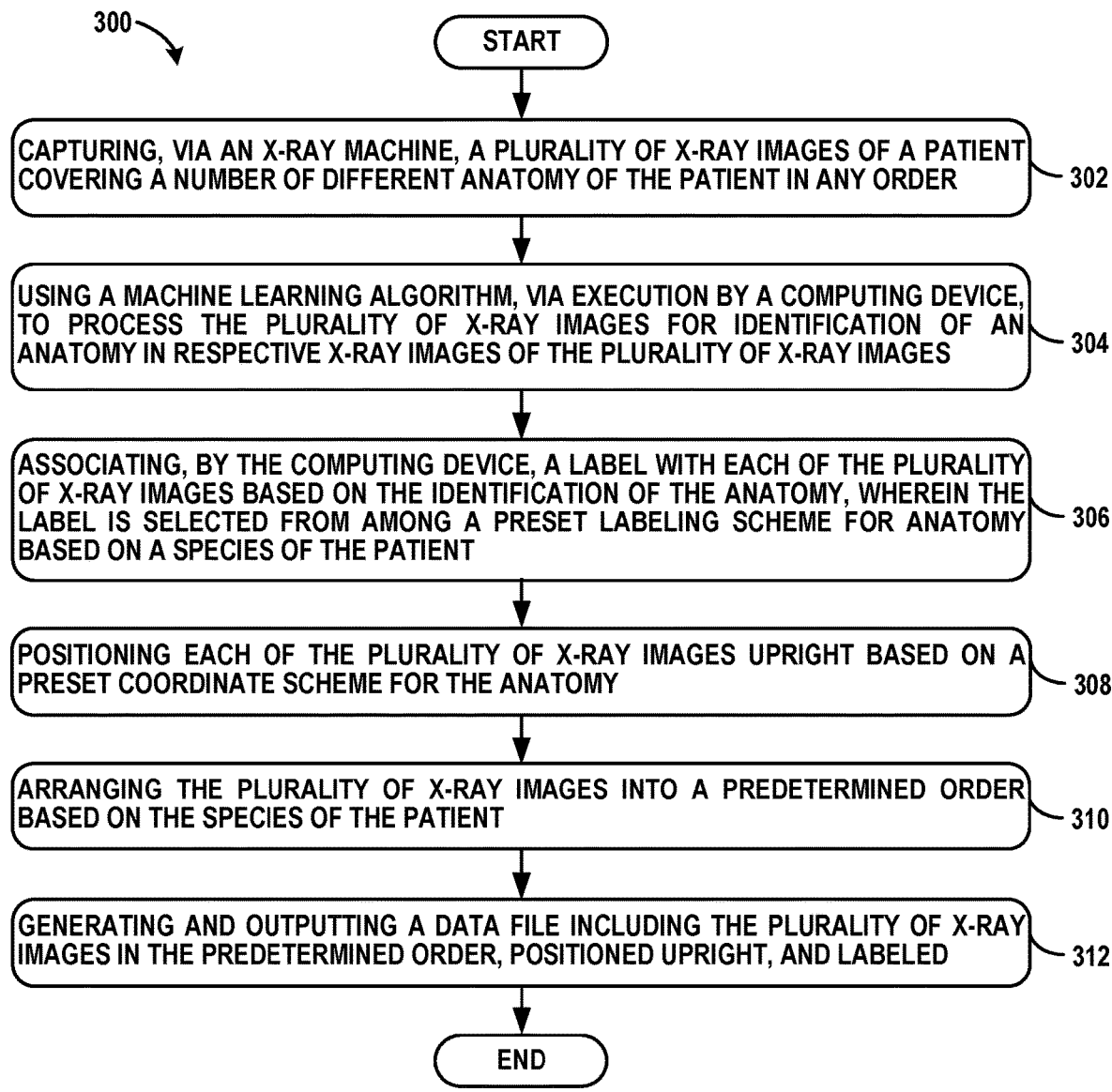
FIG. 3 shows a flowchart of another example of a method for image capture and processing, according to an example implementation.

FIG. 3 shows a flowchart of another example of a method 300 for image capture and processing, according to an example implementation. Method 300 shown in FIG. 3 presents an example of a method that could be used with the system 100 shown in FIG. 1 or the computing device 106 shown in FIG. 1, for example. Further, devices or systems may be used or configured to perform logical functions presented in FIG. 3. In some instances, components of the devices and/or systems may be configured to perform the functions such that the components are actually configured and structured (with hardware and/or software) to enable such performance. In other examples, components of the devices and/or systems may be arranged to be adapted to, capable of, or suited for performing the functions, such as when operated in a specific manner. Method 300 may include one or more operations, functions, or actions as illustrated by one or more of blocks 302-312. Although the blocks are illustrated in a sequential order, these blocks may also be performed in parallel, and/or in a different order than those described herein. Also, the various blocks may be combined into fewer blocks, divided into additional blocks, and/or removed based upon the desired implementation.

It should be understood that for this and other processes and methods disclosed herein, flowcharts show functionality and operation of one possible implementation of present examples. In this regard, each block or portions of each block may represent a module, a segment, or a portion of program code, which includes one or more instructions executable by a processor for implementing specific logical functions or steps in the process. The program code may be stored on any type of computer readable medium or data storage, for example, such as a storage device including a disk or hard drive. Further, the program code can be encoded on a computer-readable storage media in a machine-readable format, or on other non-transitory media or articles of manufacture. The computer readable medium may include non-transitory computer readable medium or memory, for example, such as computer-readable media that stores data for short periods of time like register memory, processor cache and Random Access Memory (RAM). The computer readable medium may also include non-transitory media, such as secondary or persistent long term storage, like read only memory (ROM), optical or magnetic disks, compact-disc read only memory (CD-ROM), for example. The computer readable media may also be any other volatile or non-volatile storage systems. The computer readable medium may be considered a tangible computer readable storage medium, for example.

In addition, each block or portions of each block in FIG. 3, and within other processes and methods disclosed herein, may represent circuitry that is wired to perform the specific logical functions in the process. Alternative implementations are included within the scope of the examples of the present disclosure in which functions may be executed out of order from that shown or discussed, including substantially concurrent or in reverse order, depending on the functionality involved, as would be understood by those reasonably skilled in the art.

At block 302, the method 300 includes capturing, via the x-ray machine 102, the plurality of x-ray images 104 of a patient covering a number of different anatomy of the patient in any order.

At block 304, the method 300 includes using the machine learning algorithm 132, via execution by the computing device 106, to process the plurality of x-ray images 104 for identification of an anatomy in respective x-ray images of the plurality of x-ray images 104.

At block 306, the method 300 includes associating, by the computing device 106, a label with each of the plurality of x-ray 104 images based on the identification of the anatomy, and the label is selected from among the preset labeling scheme 134 for anatomy based on a species of the patient.

At block 308, the method 300 includes positioning each of the plurality of x-ray images upright based on the preset coordinate scheme 136 for the anatomy.

At block 310, the method 300 includes arranging the plurality of x-ray images into a predetermined order based on the species of the patient.

At block 312, the method 300 includes generating and outputting the data file 120 including the plurality of x-ray images in the predetermined order, positioned upright, and labeled.

Figure 4:
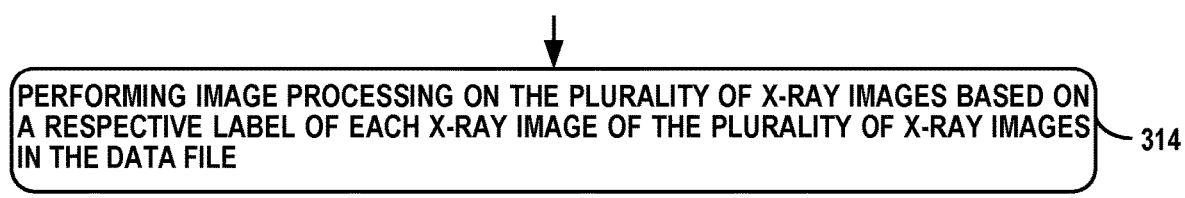
FIG. 4 shows a flowchart of additional functions that may be used with the method in FIG. 3, according to an example implementation.

FIG. 4 shows a flowchart of additional functions that may be used with the method 300 in FIG. 3, according to an example implementation. For example, at block 314, functions include performing image processing on the plurality of x-ray images based on a respective label of each x-ray image of the plurality of x-ray images in the data file 120. For example, image processing varies based on the content of the x-ray.

Figure 5:
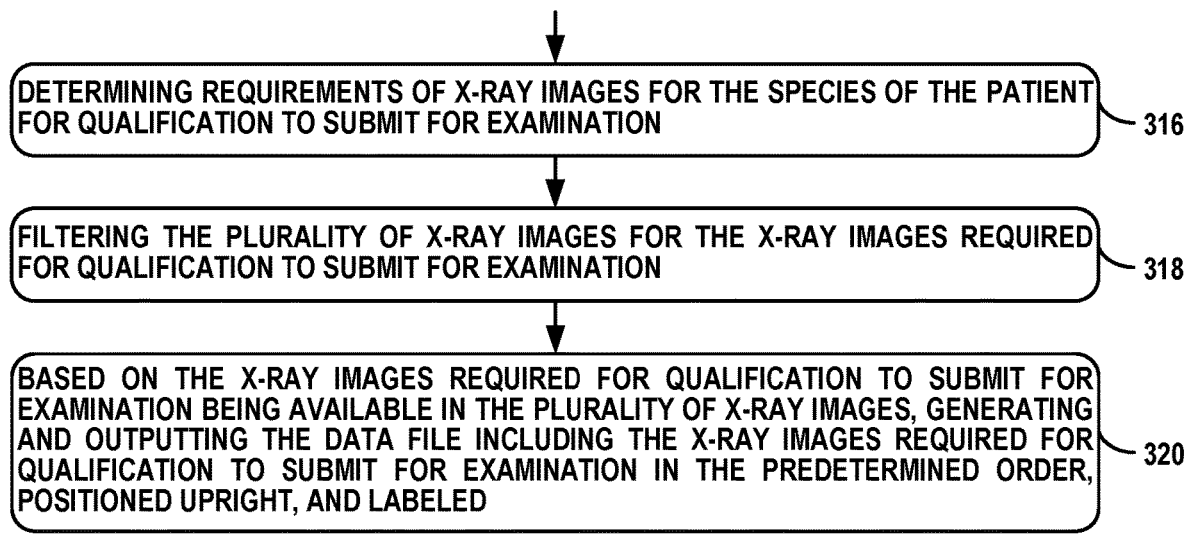
FIG. 5 shows another flowchart of additional functions that may be used with the method in FIG. 3, according to an example implementation.

FIG. 5 shows a flowchart of additional functions that may be used with the method 300 in FIG. 3, according to an example implementation. For example, at block 316, functions include determining requirements of x-ray images for the species of the patient for qualification to submit for examination. As mentioned above, the computing device 106 may access the examination requirements database 126 to determine all x-ray images needed for a specific study. Then, at block 318, functions include filtering the plurality of x-ray images for the x-ray images required for qualification to submit for examination. Following, at block 320, functions include based on the x-ray images required for qualification to submit for examination being available in the plurality of x-ray images, generating and outputting the data file 120 including the x-ray images required for qualification to submit for examination in the predetermined order, positioned upright, and labeled.

Figure 6:
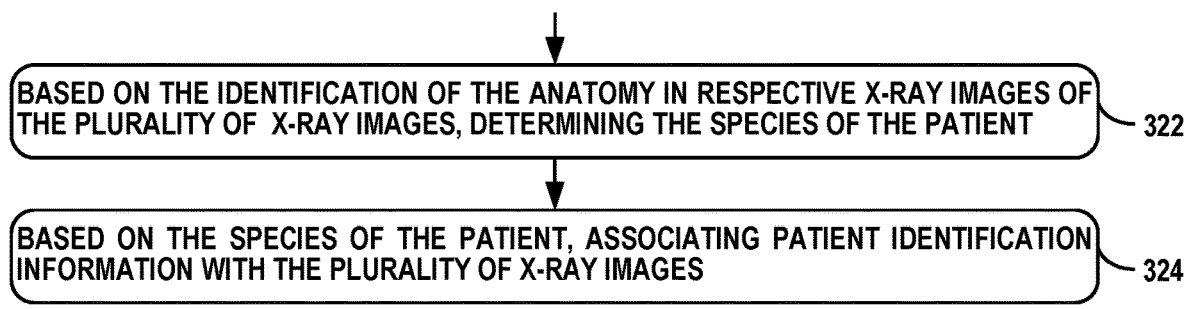
FIG. 6 shows another flowchart of additional functions that may be used with the method in FIG. 3, according to an example implementation.

FIG. 6 shows a flowchart of additional functions that may be used with the method 300 in FIG. 3, according to an example implementation. For example, at block 322, functions include based on the identification of the anatomy in respective x-ray images of the plurality of x-ray images, determining the species of the patient. Then at block 324, functions include based on the species of the patient, associating patient identification information with the plurality of x-ray images.

Figure 7:
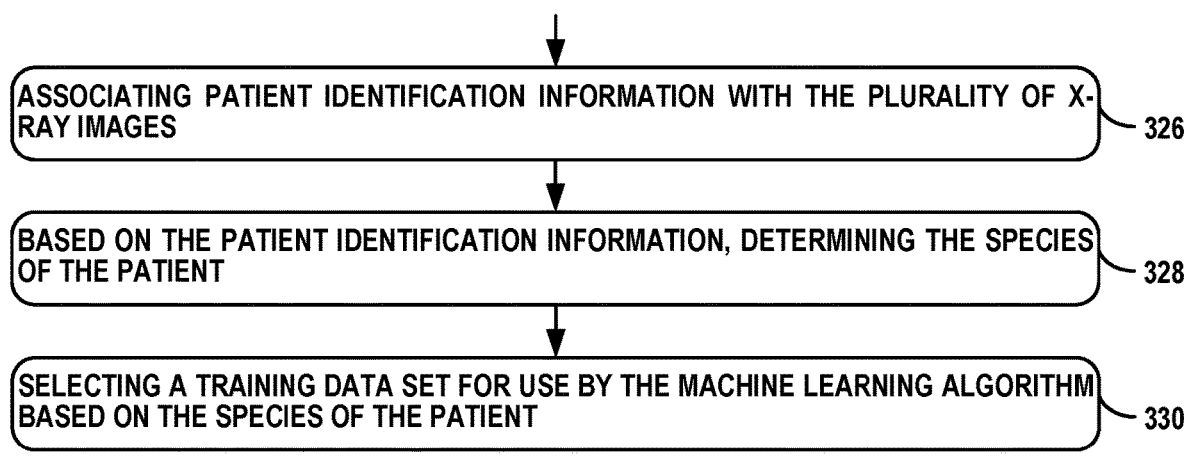
FIG. 7 shows another flowchart of additional functions that may be used with the method in FIG. 3, according to an example implementation.

FIG. 7 shows a flowchart of additional functions that may be used with the method 300 in FIG. 3, according to an example implementation. For example, at block 326, functions include associating patient identification information with the plurality of x-ray images. At block 328, functions include based on the patient identification information, determining the species of the patient. At block 330, functions include selecting a training data set for use by the machine learning algorithm 132 based on the species of the patient.

FIG. 8 shows a flowchart of additional functions that may be used with the method 300 in FIG. 3, according to an example implementation. For example, at block 332, functions include providing, via the computing device 106, feedback for proper procedure on how to capture x-rays of anatomy based on content of the plurality of x-ray images including more anatomy than intended according to the label of the plurality of x-ray images.

FIG. 9 shows a flowchart of additional functions that may be used with the method 300 in FIG. 3, according to an example implementation. For example, at block 334, functions include comparing the plurality of x-ray images with a listing of x-ray images required for a selected procedure. Then at block 336, functions include providing, via the computing device, feedback in real-time that is indicative of a missing x-ray required for the selected procedure.

FIG. 10 shows a flowchart of additional functions that may be used with the method 300 in FIG. 3, according to an example implementation. For example, in the instance in which the species of the patient is a first species, at block 338, functions include analyzing the plurality of x-ray images to determine that at least one x-ray image includes content of a second species. Then at block 340, functions include providing, via the computing device 106, feedback that is indicative of proper procedure on how to capture x-rays.

FIG. 11 shows a flowchart of additional functions that may be used with the method 300 in FIG. 3, according to an example implementation. For example, at block 342, functions include receiving information indicating an amount of exposure used by the x-ray machine to capture the plurality of x-ray images. At block 344, functions include analyzing the plurality of x-ray images to determine a quality of the plurality of x-ray images. Then at block 346, functions include providing, via the computing device 106, feedback indicative of an optimal exposure setting for the x-ray machine to capture subsequent x-ray images.

Example methods and systems described herein thus utilize rules in combination with machine learning algorithms to identify appropriate labels to apply to captured x-ray images. Prior solutions assumed that x-rays were captured in a specific shot-order and labels were simply applied according to the shot order.

Figure 12:
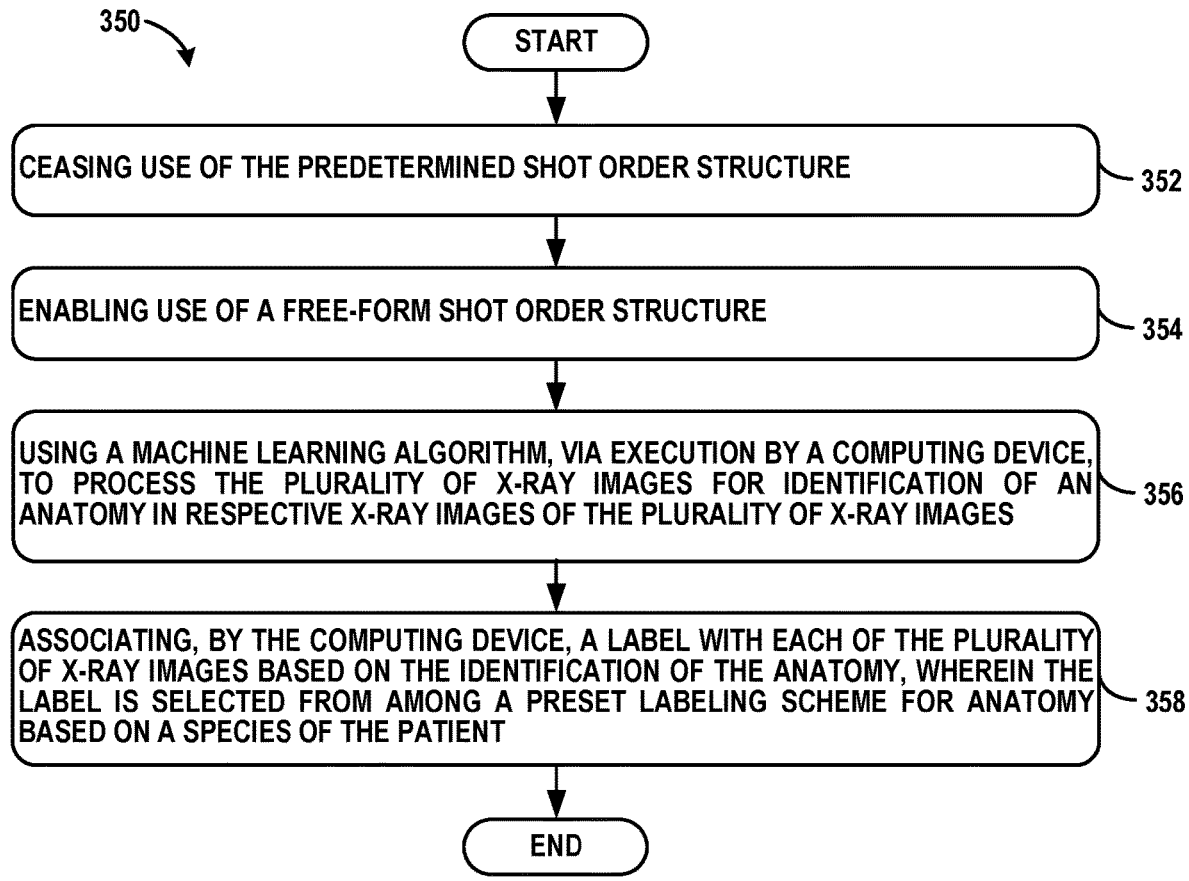
FIG. 12 shows a flowchart of an improved computer implemented method for x-ray imaging and labeling, according to an example implementation.

FIG. 12 shows a flowchart of an improved computer implemented method 350 for x-ray imaging and labeling, according to an example implementation. In one example, in a computer implemented method for x-ray imaging and labeling that includes capturing, via the x-ray machine 102, the plurality of x-ray images 104 of a patient covering a number of different anatomy of the patient in a predetermined shot order structure, and applying a preset label to each of the plurality of x-ray images according to the predetermined shot order structure independent of content of the plurality of x-ray images, the improvement includes the functions shown in FIG. 12.

At block 352, the improvement includes ceasing use of the predetermined shot order structure, and at block 354 the improvement includes enabling use of a free-form shot order structure. At block 356, the improvement includes using the machine learning algorithm 132, via execution by the computing device 106, to process the plurality of x-ray images for identification of an anatomy in respective x-ray images of the plurality of x-ray images. At block 358, the improvement includes associating, by the computing device 106, a label with each of the plurality of x-ray images 104 based on the identification of the anatomy, wherein the label is selected from among the preset labeling scheme 134 for anatomy based on a species of the patient.

In further examples, with the method 350, the predetermined shot order structure results in incorrect labeling of the plurality of x-ray images in instances in which x-ray images are not taken in the predetermined shot order structure, and the improved free-form shot order structure enables correct labeling of the plurality of x-ray images independent of an order in which the plurality of x-ray images are captured. The improved free-form shot order structure further enables correct labeling of the plurality of x-ray images in instances in which x-ray images are retaken resulting in duplicate x-ray images.

Figure 13:
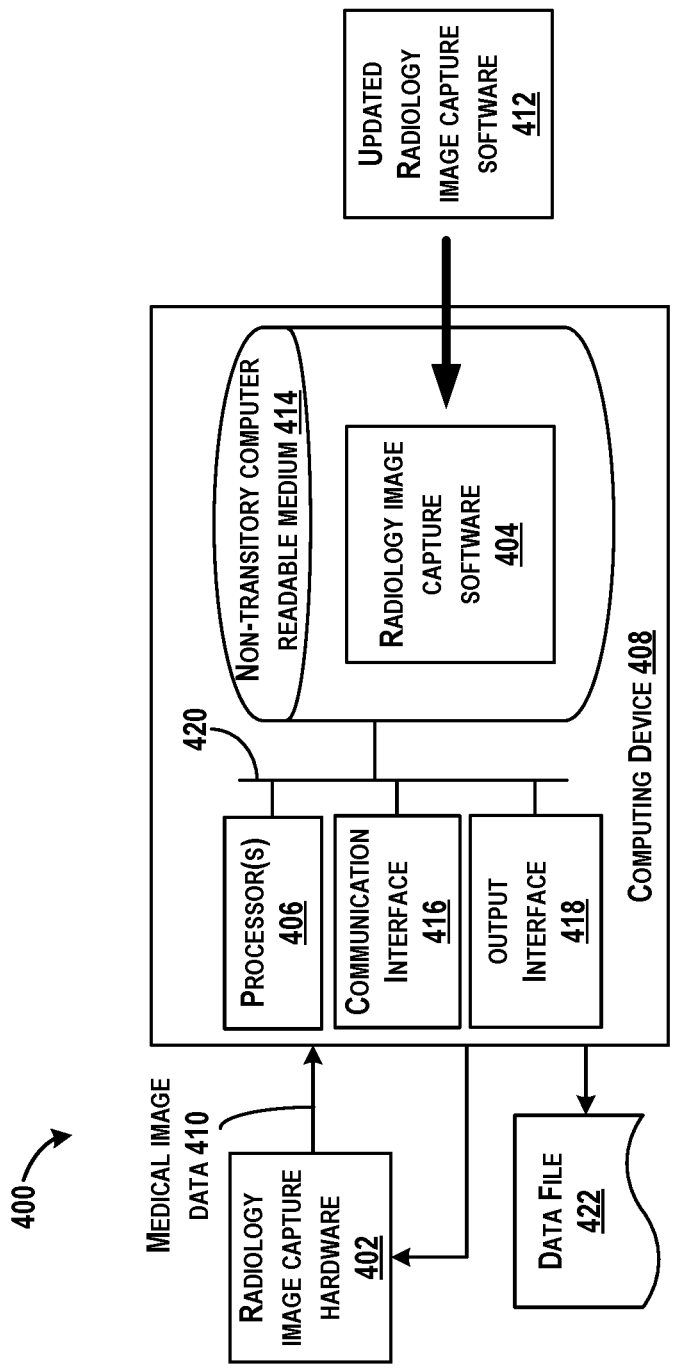
FIG. 13 illustrates an example of an improved veterinary radiology system, according to an example implementation.

FIG. 13 illustrates an example of an improved veterinary radiology system 400, according to an example implementation. In a veterinary radiology system that includes radiology image capture hardware 402 and radiology image capture software 404, wherein the radiology image capture software 404 is executable by one or more processors 406 of a computing device 408 and requires a predetermined shot order structure for capturing via the radiology image capture hardware 402 a plurality of x-ray images 410 of a patient covering a number of different anatomy so as to apply a preset label to each of the plurality of x-ray images 410 according to the predetermined shot order structure independent of content of the plurality of x-ray images, the improvement includes updated radiology image capture software 412 executable by the one or more processors 406 that enables free-form shot order structure for application of the preset labels to each of the plurality of x-ray images 410 based on content of the plurality of x-ray images 410 and independent of the free-form shot order structure. The computing device 408 stores the updated radiology image capture software 412 on non-transitory computer readable medium 414 of the computing device 408. The computing device 408 further includes a communication interface 416, an output interface 418, and a communication bus 420 similar to the computing device 106 in FIG. 1. The computing device 408 can execute the updated radiology image capture software 412 to generate and output a data file 422, similar to the data file 120 in FIG. 1.

In some other examples, embodiments can take the form of a method of upgrading the veterinary radiology system at a location where companion animal radiology images are taken. The method includes modifying or replacing the radiology image capture software 404 that had utilized a predetermined shot order structure but not a free-form shot order structure with radiology software 412 that enables free-form shot order structure.

Existing veterinarian radiology facilities require predetermined shot orders and preset image labeling, which often results in numerous mis-labeled images, and is becoming impractical for use with animals that can be difficult to position for x-ray images. Enabling free-form image capture and automated image identification and labeling is more efficient and improves results of the x-ray capture process.

By the term "substantially" and "about" used herein, it is meant that the recited characteristic, parameter, or value need not be achieved exactly, but that deviations or variations, including for example, tolerances, measurement error, measurement accuracy limitations and other factors known to skill in the art, may occur in amounts that do not preclude the effect the characteristic was intended to provide.

Different examples of the system(s), device(s), and method(s) disclosed herein include a variety of components, features, and functionalities. It should be understood that the various examples of the system(s), device(s), and method(s) disclosed herein may include any of the components, features, and functionalities of any of the other examples of the system(s), device(s), and method(s) disclosed herein in any combination or any sub-combination, and all of such possibilities are intended to be within the scope of the disclosure.

The description of the different advantageous arrangements has been presented for purposes of illustration and description, and is not intended to be exhaustive or limited to the examples in the form disclosed. Many modifications and variations will be apparent to those of ordinary skill in the art. Further, different advantageous examples may describe different advantages as compared to other advantageous examples. The example or examples selected are chosen and described in order to best explain the principles of the examples, the practical application, and to enable others of ordinary skill in the art to understand the disclosure for various examples with various modifications as are suited to the particular use contemplated.

What is claimed is:

1. A computer implemented method for x-ray imaging and labeling comprising:
   capturing, via an x-ray machine, a plurality of x-ray images of a patient covering a number of different anatomy of the patient in a predetermined shot order structure, and applying a preset label to each of the plurality of x-ray images according to the predetermined shot order structure independent of content of the plurality of x-ray images,
   ceasing use of the predetermined shot order structure;
   enabling use of a free-form shot order structure;
   using a machine learning algorithm, via execution by a computing device, to process the plurality of x-ray images for identification of an anatomy in respective x-ray images of the plurality of x-ray images; and
   associating, by the computing device, a label with each of the plurality of x-ray images based on the identification of the anatomy, wherein the label is selected from among a preset labeling scheme for anatomy based on a species of the patient.

2. The computer implemented method of claim 1, wherein the predetermined shot order structure results in incorrect labeling of one or more x-ray images of the plurality of x-ray images in instances in which the one or more x-ray images of the plurality of x-ray images were not taken in the predetermined shot order structure, and wherein the processing the plurality of x-ray images comprises correcting labeling of the one or more x-ray images of the plurality of x-ray images.

3. The computer implemented method of claim 1, wherein processing the plurality of x-ray images comprises correcting labeling of the plurality of x-ray images in instances in which x-ray images are retaken and the retaken x-ray images result in duplicate x-ray images.

4. The computer implemented method of claim 1, further comprising:
   positioning each of the plurality of x-ray images in an orientation based on a preset coordinate scheme for the anatomy.

5. The computer implemented method of claim 4, further comprising:

generating and outputting a data file including the plurality of x-ray images positioned in the orientation and labeled.

6. The computer implemented method of claim 1, further comprising:
arranging the plurality of x-ray images into a predetermined order based on the species of the patient.

7. The computer implemented method of claim 6, further comprising:
generating and outputting a data file including the plurality of x-ray images in the predetermined order and labeled.

8. The computer implemented method of claim 1, further comprising:
determining requirements of x-ray images for the species of the patient for qualification to submit for examination;
filtering the plurality of x-ray images for the x-ray images required for qualification to submit for examination; and
based on the x-ray images required for qualification to submit for examination being available in the plurality of x-ray images, generating and outputting the data file including the x-ray images required for qualification to submit for examination.

9. The computer implemented method of claim 1, further comprising:
based on the identification of the anatomy in respective x-ray images of the plurality of x-ray images, determining the species of the patient; and
based on the species of the patient, associating patient identification information with the plurality of x-ray images.

10. The computer implemented method of claim 1, further comprising:
associating patient identification information with the plurality of x-ray images;
based on the patient identification information, determining the species of the patient; and
selecting a training data set for use by the machine learning algorithm based on the species of the patient.

11. The computer implemented method of claim 1, further comprising:
providing, via the computing device, feedback for proper procedure on how to capture x-rays of anatomy based on content of the plurality of x-ray images including more anatomy than a configurable threshold according to the label of the plurality of x-ray images.

12. The computer implemented method of claim 1, wherein the further comprising:
comparing the plurality of x-ray images with a listing of x-ray images required for a selected procedure; and
providing, via the computing device, feedback that is indicative of a missing x-ray required for the selected procedure.

13. The computer implemented method of claim 1, wherein the species of the patient is a first species, the method further comprising:
analyzing the plurality of x-ray images to determine that at least one x-ray image includes content of a second species; and
providing, via the computing device, feedback that is indicative of proper procedure on how to capture x-rays.

14. The computer implemented method of claim 1, further comprising:

receiving information indicating an amount of exposure used by the x-ray machine to capture the plurality of x-ray images;
analyzing the plurality of x-ray images to determine a quality of the plurality of x-ray images; and
providing, via the computing device, feedback indicative of an optimal exposure setting for the x-ray machine to capture subsequent x-ray images.

15. In a veterinary radiology system that includes radiology image capture hardware and radiology image capture software, wherein the radiology image capture software is executable by one or more processors of a computing device and requires a predetermined shot order structure for capturing via the radiology image capture hardware a plurality of x-ray images of a patient covering a number of different anatomy so as to apply a preset label to each of the plurality of x-ray images according to the predetermined shot order structure independent of content of the plurality of x-ray images, a non-transitory computer-readable media having stored therein instructions executable by the one or more processors of the computing device to perform functions comprising:
updating radiology image capture software executable by the one or more processors that enables free-form shot order structure for application of the preset labels to each of the plurality of x-ray images based on content of the plurality of x-ray images and independent of the free-form shot order structure.

16. The veterinary radiology system of claim 15, further comprising:
using a machine learning algorithm, via execution by the computing device, to process the plurality of x-ray images for identification of an anatomy in respective x-ray images of the plurality of x-ray images.

17. The veterinary radiology system of claim 16, further comprising:
associating, by the computing device, a label with each of the plurality of x-ray images based on the identification of the anatomy, wherein the label is selected from among the preset labels.

18. The veterinary radiology system of claim 15, further comprising:
positioning each of the plurality of x-ray images in an orientation based on a preset coordinate scheme for the anatomy; and
generating and outputting a data file including the plurality of x-ray images positioned in the orientation and labeled.

19. The veterinary radiology system of claim 15, further comprising:
arranging the plurality of x-ray images into a predetermined order based on the species of the patient; and
generating and outputting a data file including the plurality of x-ray images in the predetermined order and labeled.

20. The veterinary radiology system of claim 15, further comprising:
correcting labeling of the plurality of x-ray images in instances in which x-ray images are retaken and the retaken x-ray images result in duplicate x-ray images.

* * * * *